(12) United States Patent
McCarthy et al.

(10) Patent No.: US 11,389,306 B2
(45) Date of Patent: Jul. 19, 2022

(54) SEAL AND SUSPENSION LINER FOR A PROSTHESIS

(71) Applicant: Blatchford Products Limited, Basingstoke (GB)

(72) Inventors: Joseph McCarthy, Fareham (GB); Alan McDougall, Fareham (GB); Ana Gallego Murillo, Greater London (GB)

(73) Assignee: BLATCHFORD PRODUCTS LIMITED, Basingstoke (GB)

( * ) Notice: Subject to any disclaimer, the term of this patent is extended or adjusted under 35 U.S.C. 154(b) by 2 days.

(21) Appl. No.: 16/318,203

(22) PCT Filed: Jul. 18, 2017

(86) PCT No.: PCT/GB2017/052108
§ 371 (c)(1),
(2) Date: Jan. 16, 2019

(87) PCT Pub. No.: WO2018/015736
PCT Pub. Date: Jan. 25, 2018

(65) Prior Publication Data
US 2019/0262146 A1 Aug. 29, 2019

(30) Foreign Application Priority Data
Jul. 18, 2016 (GB) ...................... 1612436

(51) Int. Cl.
*A61F 2/78* (2006.01)
*A61F 2/60* (2006.01)
*A61F 2/80* (2006.01)

(52) U.S. Cl.
CPC .............. *A61F 2/7812* (2013.01); *A61F 2/60* (2013.01); *A61F 2/78* (2013.01); *A61F 2/80* (2013.01); *A61F 2002/7837* (2013.01)

(58) Field of Classification Search
CPC ................................ A61F 2/7812; A61F 2/80
See application file for complete search history.

(56) References Cited

U.S. PATENT DOCUMENTS

| | | | | |
|---|---|---|---|---|
| 5,007,937 A | * | 4/1991 | Fishman | .................. A61F 2/80 623/34 |
| 6,645,253 B2 | | 11/2003 | Caspers | |

(Continued)

FOREIGN PATENT DOCUMENTS

| | | |
|---|---|---|
| EP | 2254526 B1 | 9/2013 |
| GB | 2486817 A | 6/2012 |

(Continued)

OTHER PUBLICATIONS

Office Action dated Apr. 2, 2019 in GB Application No. 1612436.4.
(Continued)

*Primary Examiner* — Bruce E Snow
(74) *Attorney, Agent, or Firm* — Panitch Schwarze Belisario & Nadel LLP (57) ABSTRACT

A seal (24) for a suspension liner (30) comprises a tubular substrate having an axis and a plurality of fins (26) projecting radially from the substrate. The tubular substrate has an axis and the fins (26) nm reciprocate axially as they nm peripherally around the substrate. The seal (26) may be mounted on the suspension (30) liner or fins may be integrally formed on the outer surface of the liner.

13 Claims, 6 Drawing Sheets

(56) References Cited

U.S. PATENT DOCUMENTS

| | | | |
|---|---|---|---|
| 6,726,726 B2 | 4/2004 | Caspers | |
| 8,956,422 B2* | 2/2015 | Halldorsson | A61F 2/7812 |
| | | | 623/36 |
| 10,322,016 B2* | 6/2019 | Birgisdottir | A61F 2/7812 |
| 2004/0122528 A1 | 6/2004 | Egilsson | |
| 2011/0264239 A1 | 10/2011 | Egilsson et al. | |
| 2012/0116538 A1 | 5/2012 | Patterson | |
| 2015/0096931 A1* | 4/2015 | Jensen | B01D 29/21 |
| | | | 210/437 |
| 2015/0105867 A1* | 4/2015 | Novak | A61F 2/80 |
| | | | 623/36 |
| 2017/0105853 A1* | 4/2017 | Jonsson | A61F 2/80 |

FOREIGN PATENT DOCUMENTS

| | | |
|---|---|---|
| WO | 0170147 A2 | 9/2001 |
| WO | 02067825 A2 | 9/2002 |
| WO | 2009093020 A2 | 7/2009 |
| WO | 2015073793 A1 | 5/2015 |
| WO | 2016015024 A1 | 1/2016 |

OTHER PUBLICATIONS

Search Report dated Dec. 28, 2016 in GB Application No. 1612436.4.

Int'l Search Report and Written Opinion dated Oct. 18, 2017 in Int'l Application No. PCT/GB2017/052108.

* cited by examiner

SEAL AND SUSPENSION LINER FOR A PROSTHESIS

CROSS-REFERENCE TO RELATED APPLICATION

This application is a Section 371 of International Application No. PCT/GB2017/052108, filed Jul. 18, 2017, which was published in the English language on Jan. 25, 2018 under International Publication No. WO 2018/015736 A1, which claims priority under 35 U.S.C. § 119(b) to British Patent Application No. 1612436.4, filed Jul. 18, 2016, the disclosures of which are incorporated herein by reference.

TECHNICAL FIELD

The present invention relates to a suspension liner for a lower limb prosthesis. In particular, the present invention relates to a seal and a suspension liner bearing such a seal for use in maintaining a reduced pressure in a socket when used with a prosthesis.

BACKGROUND TO THE INVENTION AND PRIOR ART

A prosthesis can be attached to a residual limb in the following manner. A hollow hard socket is custom made to accommodate the shape of the residual limb. The socket includes means for attaching the prosthesis to the socket. Before inserting the residual limb into the socket a soft flexible liner is typically donned on the residual limb to serve as an interface between the residual limb and the socket. The liner is typically made from an air impermeable material such as silicone.

An intimate fit is required between the residual limb, the liner and the socket. This close fit is required to prevent relative motion between the socket and liner and the residual limb, to prevent irritation of the skin and other soft tissue of the residual limb. The intimate fit better distributes forces on the residual limb when weight is applied to the prosthesis via the socket. For a lower limb prosthesis, this will occur when the prosthesis is in contact with ground, for example when standing and during the stance phase of the gait cycle. Additionally, air expulsion, typically via a one-way valve, achieved as a result of the intimate fit is used to contribute to the formation of a reduced pressure/(partial) vacuum between the liner and the socket so that the prosthesis remains suspended from the residual limb. For a lower limb prosthesis, this will occur during the swing phase of the gait cycle, when the limb is not in contact with the ground. Hence, the presence of a low pressure/vacuum between the socket and the residual limb/liner combination is a desirable feature of such prostheses.

A number of methods have been used to maintain a reduced pressure between the socket and the liner during the swing phase. For example, our patent application published as GB-A-2486817 describes a vacuum assisted suspension device for a prosthesis comprising an air impermeable socket shaped to receive a limb portion. The socket has a peripheral edge and includes an evacuation port and a non-return valve associated with the evacuation port. The evacuation port and return valve are arranged to maintain a vacuum between the socket and the limb portion when the latter is received by the socket. The device includes a sleeve which spans the peripheral edge of the socket and the limb portion. When air is evacuated/expelled from the socket via the evacuation port the sleeve acts as a seal.

As a further example, our patent application published as EP-A-2254526 describes a vacuum-assisted liner system for the socket of a limb prosthesis which secures the prosthesis to a residual body portion. The system includes a flexible liner made of an impermeable material, at least a distal part of the liner being porous to allow the transport of air and fluid directly away from the residual body portion to the outer surface of the liner. A fabric distribution layer is located over the liner and between the liner and the socket to allow transmission of such extracted air and fluid laterally over the liner to an evacuation port in the socket.

There are other known methods of sealing the cavity between the exterior of the suspension liner and the interior of the socket. For example the liner may include peripheral seals which bear on the interior wall of the socket to form an airtight seals. US-A1-2011/0264239 describes a suspension liner sleeve having an elongate, generally conical body. The liner sleeve includes a plurality of resilient seal elements protruding radially from the liner sleeve outer surface. A pair of adjacent annular recesses may be located above and below each of the seal elements. When the limb and liner are inserted into the socket the seal deforms against the force exerted by the socket into its associated annular recess and seals against the interior of the socket. A number of alternate seal designs are described in that document. Other prior art publications include U.S. Pat. Nos. 6,726,726, 6,645,253, WO-A-01/070147 and WO-A-02/067825.

US-A1-2015/0105867 describes a gel liner with a patterned texture on its outer surface and a socket with a complementary and interlocking patterned texture on its inner surface.

US-A1-2012/0116538 describes a liner a medial zone of which comprises ridges aligned with a posterior portion of an associated articulating zone.

WO-A1-2016/015024 describes a system and method for sealing a prosthetic socket.

WO-A1-2015/073793 describes a seal component selectively placed over an outer surface of a suspension liner having a plurality of seal bands.

A disadvantage of existing seal products and liners bearing such seals is that the seal makes the liner difficult to don. This is because of the thickness of the seal and its rigidity which makes stretching of the corresponding portion of the liner difficult. Additionally, once the liner is donned it can cause increased pressure on the residuum in the area of the seal, which can lead to irritation of the skin and adjacent tissue. This is particularly the case where the seal is positioned against bony areas and neuromas. This problem has been mitigated somewhat by providing seals which can be disposed at different heights along the length of the liner, thereby avoiding sensitive areas of the skin. However, these seals are typically relatively inelastic and exert a high hoop-stress around the limb portion where they are positioned. In addition, it is not always possible to locate the seal at a position along the liner without impinging on a sensitive area of the residual limb.

The present invention provides an improved seal and a liner bearing that seal.

SUMMARY OF INVENTION

According to a first aspect of the invention, there is provided a seal for a suspension liner, the seal comprising: a tubular substrate having an axis; and one or more fins projecting radially from the substrate and running peripherally around the substrate, wherein the or at least one of the fins reciprocates axially as it runs peripherally around the substrate.

The wave form of the fins of the seal may provide one or more of the following advantages:
- Natural flow of movements of material in donning, thereby creating a more robust seal with the socket.
- Natural flow of movements of material in doffing the residual limb from the socket interface made with less resistance from direction of frictional forces.
- Easier circumferential stretch (producing lower hoop-stresses) than would be the case with a simple circumferential fin/seal.
- Easier donning/doffing due to the easier circumferential stretch of the "wavy seal".
- The wave shape of the seal allows the positioning of sensitive areas away from rigid or thickened fin regions, in other words outside the seals, between the waves.

The fin or fins may be endless. All of the fins may reciprocate axially as they run peripherally around the substrate. The fin or fins may reciprocate sinusoidally around the substrate.

A plurality of or all of the fins may be parallel to each other and edges of the substrate may be parallel to the fins.

The fin or fins may have a triangular, rounded, saw-tooth or other shaped profile or a mixture of such profiles.

According to a second aspect of the invention there is provided a seal for a suspension liner, the seal comprising: a tubular substrate extending along an axis; and a plurality of fins projecting from the substrate and running circumferentially around the substrate, wherein at least one of the fins runs around the substrate and reciprocates between the intersection of a pair of planes which pass through first and second points along the axis and which are perpendicular to the axis, the first and second points being separated by a distance greater than the width of the fin.

According to a third aspect of the invention there is provided a seal for a suspension liner, the seal comprising: a tubular substrate; and a plurality of fins projecting from the substrate and running circumferentially around the substrate, wherein the length of at least one of the fins is greater than the shortest circumference around the substrate passing through any point of that fin.

The seals as described above may be is made from a resiliently elastic material.

According to a further aspect of the invention there is provided a suspension liner comprising an elongate, generally frusto-conical or cylindrical body which is closed at a first end and open at a second end, the body bearing a seal as described above at a position between the open and closed ends of the body.

According to a further aspect of the invention there is provided a suspension liner comprising an elongate, generally frusto-conical or cylindrical body having an axis and one or more fins projecting radially from the body and running peripherally around the body, wherein the fin or one or more of the fins reciprocate axially as it/they run peripherally around the body.

The fins may be grouped together over a minority of an axial length of the liner or may be spaced apart over a majority of an axial length of the liner.

The liner may be perforated distal and/or proximal to the fin or fins.

BRIEF DESCRIPTION OF THE DRAWINGS

The present invention will now be described by way of example only, and with reference to the accompanying drawings in which.

DETAILED DESCRIPTION OF THE DRAWINGS

Figure 1A:
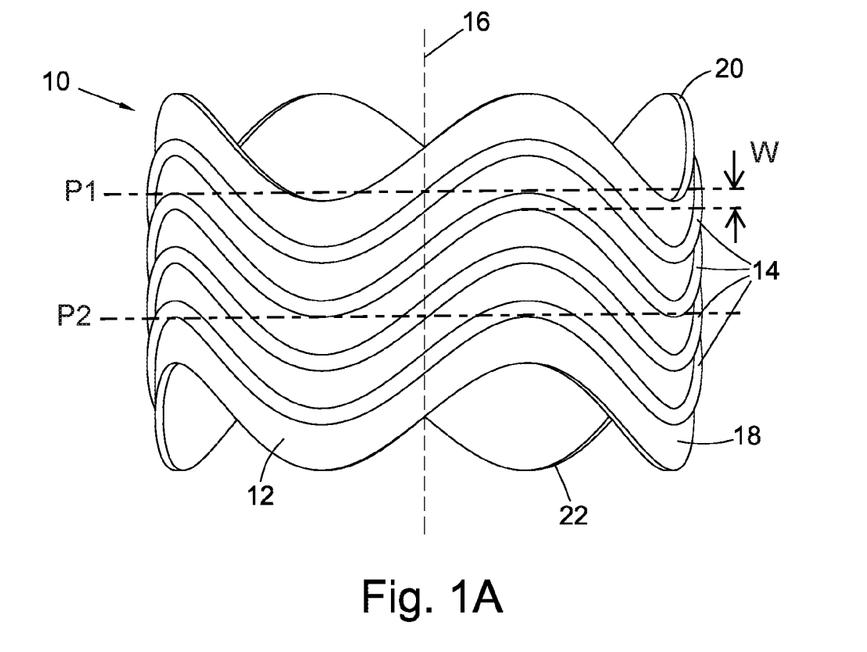
FIG. 1A is a side view of a seal for a suspension liner in accordance with a first embodiment of the invention.
Figure 1B:
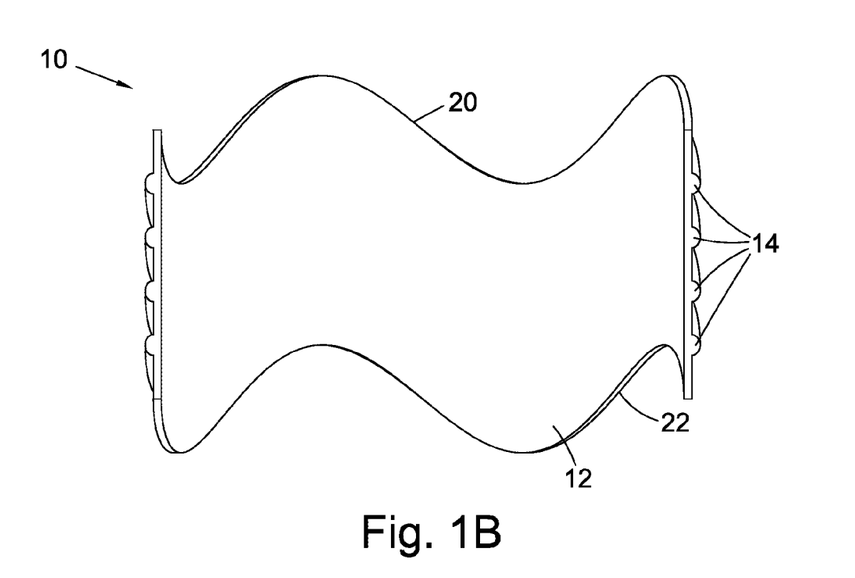
FIG. 1B is a cross-section view of the seal of FIG. 1A.

Referring to FIGS. 1A and 1B, a seal 10 for a suspension liner in accordance with the invention has a substrate 12 and a plurality of fins 14 projecting radially from the substrate 10. The seal 10 is made from a flexible silicone material, for example by moulding. The substrate 12 is generally tubular, i.e., it is open at both ends and is made such that when viewed from above it has a round cross section around a longitudinal axis 16. However, since the seal 10 is made from flexible silicone material it is easily deformed and does not necessarily maintain a tubular shape. The substrate 12 should be as thin as possible to be able to support the fins 14 and may have a thickness of around 0.5 mm. The inner diameter of the tubular substrate 12 can be varied in order to accommodate limbs of different girth. For example, this diameter may vary between 20 cm and 55 cm for lower extremity prostheses and the range would be smaller when used in conjunction with upper extremity liners. The seals can also be attached peripherally around edges of an inner wall of a hip dis-articulation socket, a shoulder dis-articulation socket or to an orthotic device.

There are four endless fins 14 running peripherally around the substrate 12. The fins 14 are 'wavy' in that the fins 14 reciprocate axially as they run peripherally around the substrate 12. The wavy shape of the fins 14 mimics a sinusoidal curve as the fins 14 pass around the substrate 12. Each fin 14 extends longitudinal (parallel to axis 16) along the substrate 12 between positions which intersect with a pair of planes (P1, P2) which pass through first and second points along the axis 16 and which are perpendicular to the axis 16, the first and second points being separated by a distance greater than the width (W) of the fin 14. In other words, the fins 14 do not run directly around the substrate 12 but deviate from a plane running perpendicular to the axis 16.

The fins 14 in FIGS. 1A and 1B have a round profile. The fins 14 project radially from an outer surface 18 of the substrate 12 by around 5 mm and have a width of around 3 mm. As can be seen from FIGS. 1A and 1B, the fins 14 run parallel to each other as they circle the substrate 12. Upper 20 and lower 22 edges of the substrate 12 run parallel to the fins 14 such that they also follow a wavy sinusoidal path.

In use, the seal 10 is placed over a liner (as described below) before the liner and seal 12 are inserted into a prosthetic socket. Since the fins 14 have a raised profile, the fins 14 in use press against an inner wall of the prosthetic socket to create an airtight seal with that wall. The liner and seal combination is typically used with a socket incorporating an expulsion valve placed distal to the position of the seal, to provide for expulsion of air from the socket cavity. The expulsion valve may optionally be connected to an external vacuum source. The fins 14 can be constructed using silicone or another material having a single durometer or a variety of durometers throughout their profile and which may be the same or different to the durometer of the substrate 12.

Figure 2A:
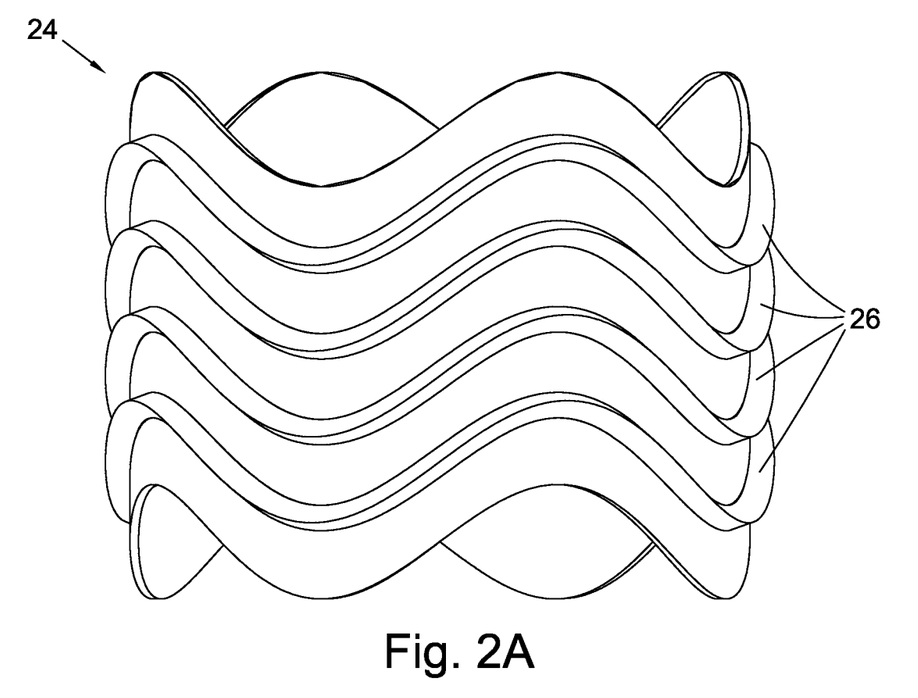
FIG. 2A is a side view of a seal according to a second embodiment of the invention.
Figure 2B:
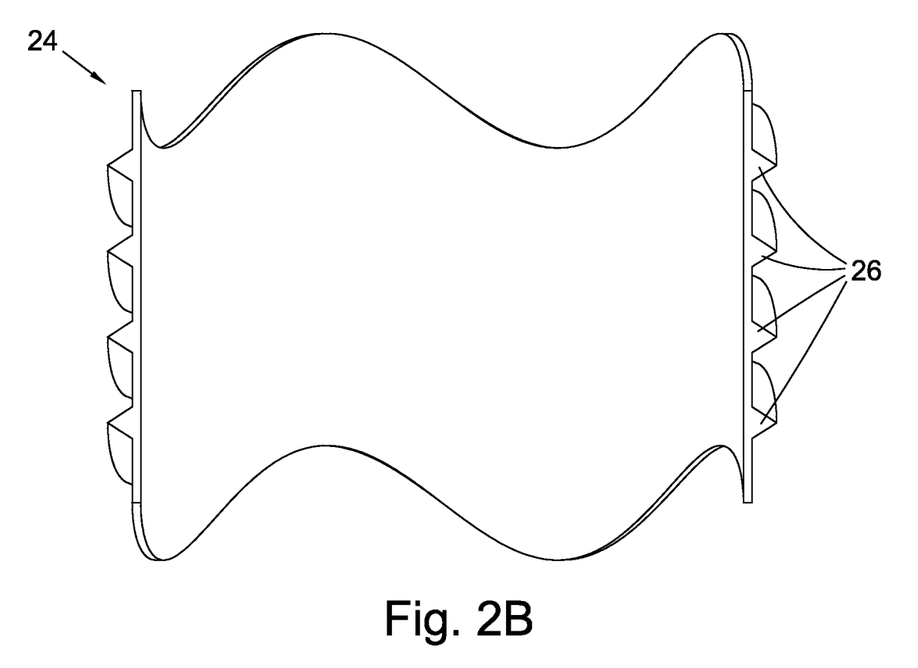
FIG. 2B is a cross-section view of the seal of FIG. 2A.

FIG. 2A is a side view of a seal 24 according to a second embodiment of the invention and FIG. 2B is a cross-section thereof. The seal 24 has a similar overall shape to the seal 10 of FIGS. 1A and 1B, however the fins 26 of the seal 24 have a triangular profile, rather than the rounded profile of the fins 14 of the seal 10.

Figure 3A:
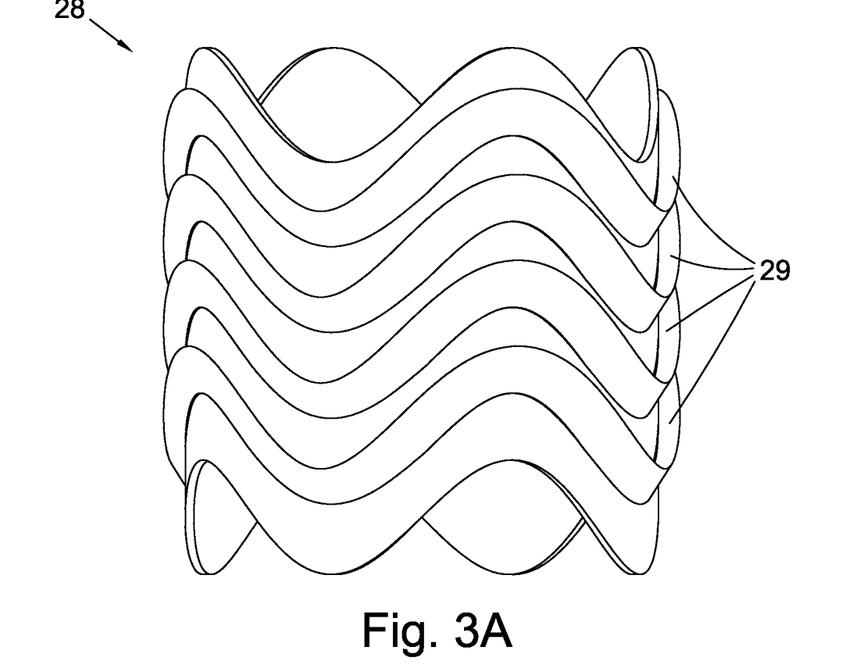
FIG. 3A is a side view of a seal according to a third embodiment of the invention.
Figure 3B:
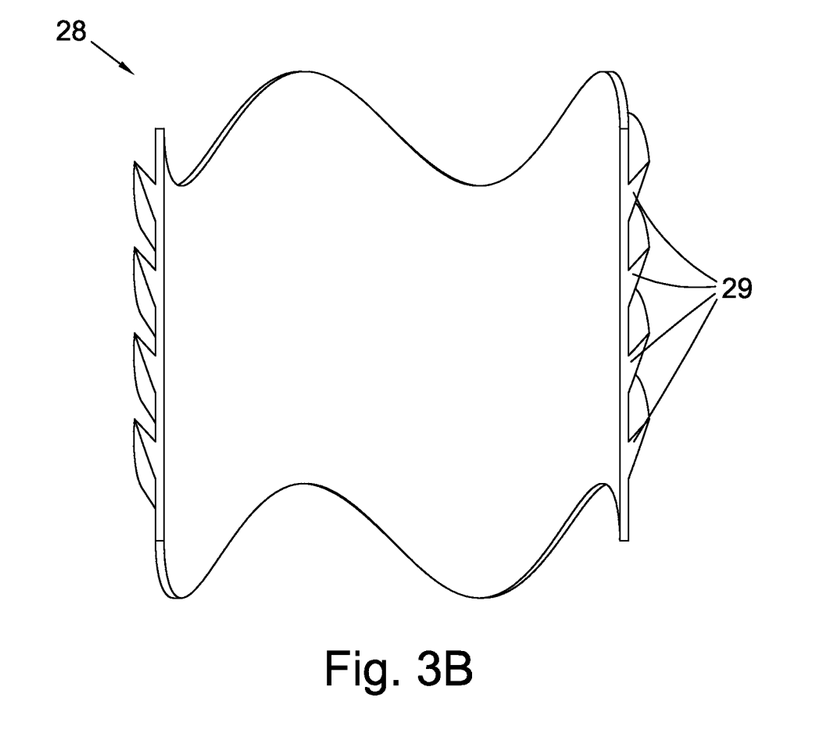
FIG. 3B is a cross-section view of the seal of FIG. 2A.

FIG. 3A is a side view of a seal 28 according to a second embodiment of the invention and FIG. 3B is a cross-section thereof. The seal 28 has a similar overall shape to the seal 10 of FIGS. 1A and 1B, however the fins 29 of the seal 28 have a saw-tooth profile, rather than the rounded profile of the fins 14 of the seal 10 of FIGS. 1A and 1B and the triangular profile of the fins 26 of the seal 24 of FIGS. 2A and 2B.

Figure 4:
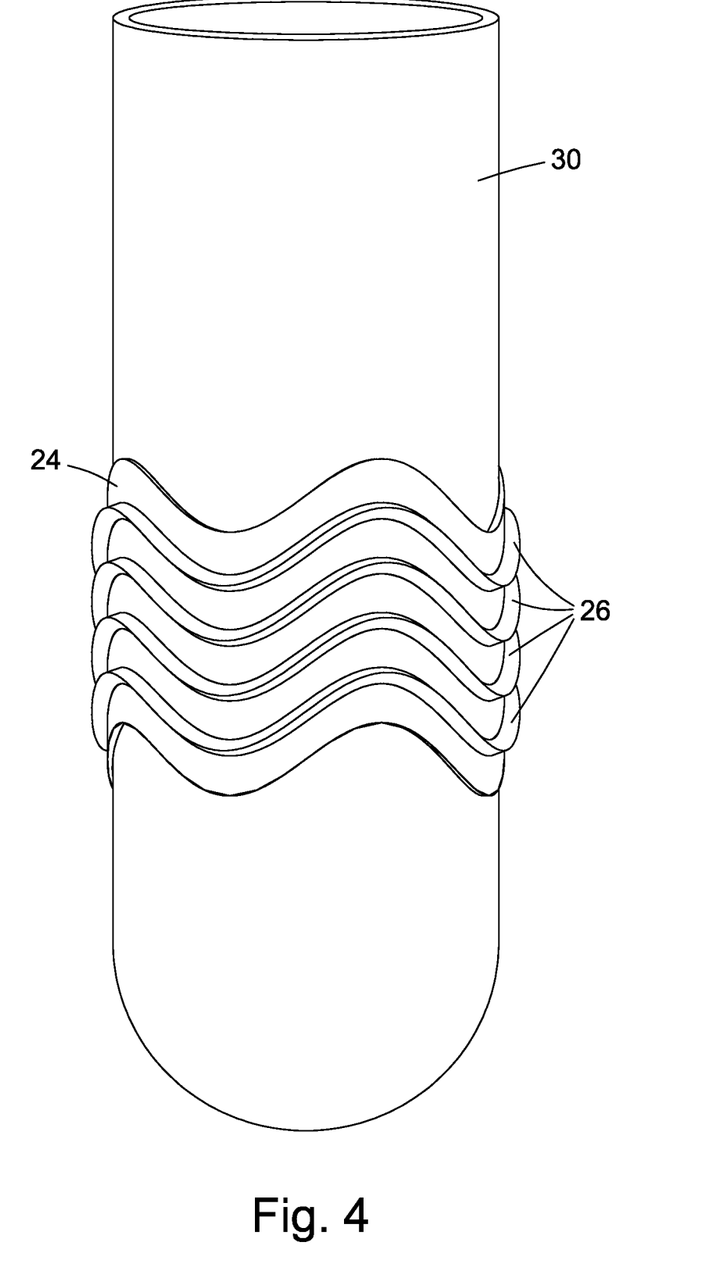
FIG. 4 is a perspective view of a suspension liner on which is mounted the seal shown in FIGS. 2A and 2B.

FIG. 4 is a perspective view of a suspension liner 30 on which is mounted the seal 24 shown in FIGS. 2A and 2B. The suspension liner 30 may be a 'standard' liner, typically made from a non-porous/air impermeable material, or may be a perforated liner, for example, as described in our granted patent EP-B-2653138, to assist with sweat/moisture management. Alternatively the liner in part or whole may be made of a porous material. When the seal 24 is mounted on a perforated liner (to be used with a vacuum suspension system) the perforations will typically be in the distal portion of the liner beyond the seal. Additionally it is conceivable to perforate the liner both proximal and distal to the seals, as long as the area of the liner 30 where the seal is mounted is sufficient to be airtight against the amputee's skin and the seal 24 is airtight against the socket wall in the region of the fins 26.

The liner 30 is flexible and is to be fitted over the body portion (whether upper or lower limb) and made of a material impermeable to air. The liner may optionally be covered with a fabric layer, to ease insertion and removal from the socket. When the seal 24 is placed over the liner 30 it is positioned such that it engages with an inner wall of a socket to provide a sound seal with the socket and it also to be positioned such that the fins 26 do not align with a sensitive part of the amputee's limb, thereby avoiding applying pressure to such a sensitive area. Hence an advantage of having a separate seal 24 and liner 30 provides for easy customisation and repositioning of the seal 24 on the liner 30. Also, since the fins 26 are subject to greater lateral forces on insertion into and removal from the socket than the liner 30, not adhering the seal 24 to the liner 30 allows for easily replacement of the seal 24 whilst the liner 30 itself maintains its structural integrity.

The seal 24 can be fixed in place on the liner 30 by applying an adhesive (e.g., liquid adhesive or double-sided tape) or the seal 24 can be held in place merely by means of the compressive force which it applies to the liner 30 when worn on the limb. Attaching the seal 24 to the liner 30 using adhesive may be performed by spreading a liquid adhesive on the seal 24 and/or the liner 30 or the adhesive may be applied to these parts within micro-spheres which burst when the seal 24 is pushed against a chosen part of the liner 30. Alternatively other permanent or semi-permanent attachment means may be used.

Figure 5:
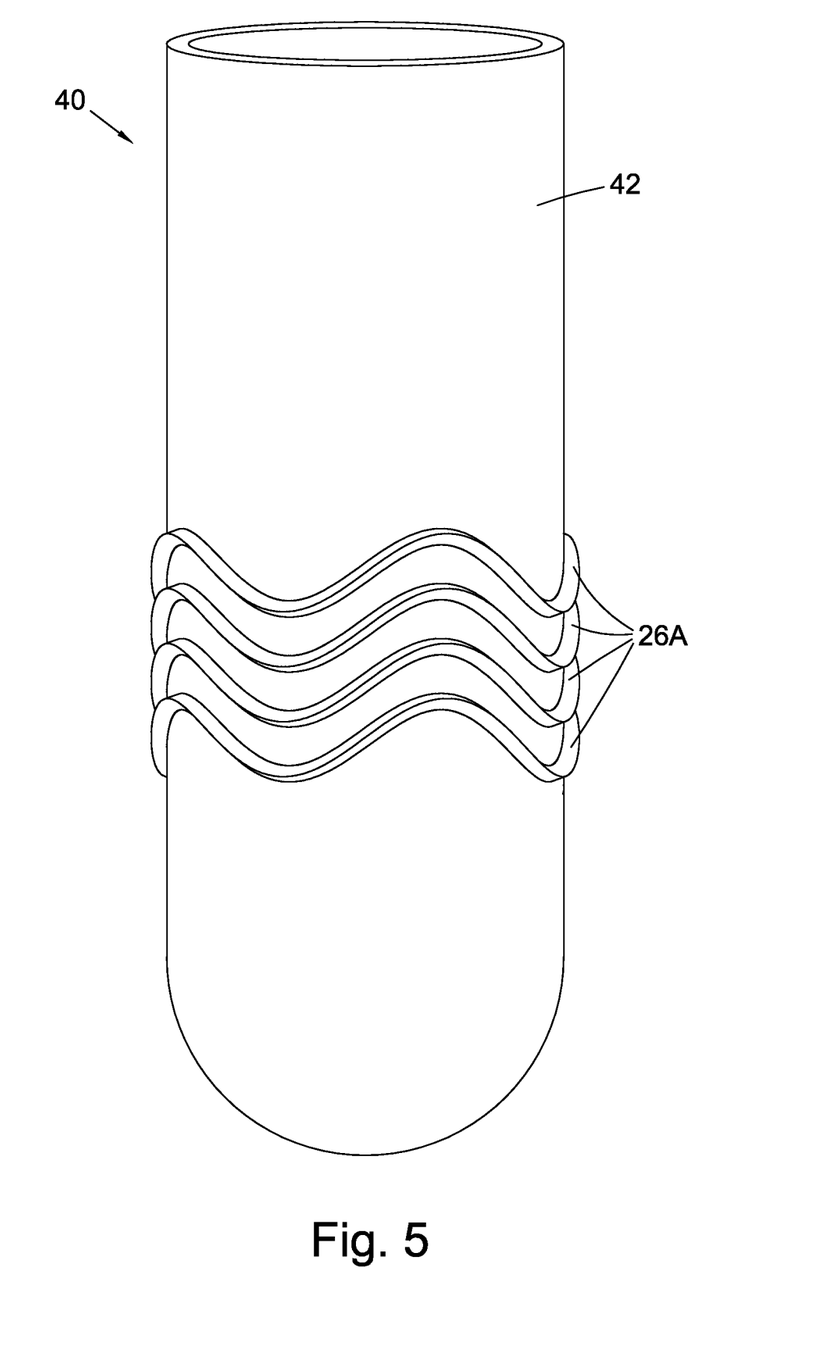
FIG. 5 is a perspective view of a suspension liner incorporating fins having a profile the same as the fins shown in FIGS. 2A and 2B.

FIG. 5 is a perspective view of a suspension liner 40 comprising a liner body 42 and incorporating fins 26A as shown in FIGS. 2A and 2B. The liner 40 has a similar appearance to the liner 30 of FIG. 3 other than the integral formation of the fins 26A together with the liner body 42 of the suspension liner 40.

Whilst FIGS. 4 and 5 have been described as including fins 26, 26A having a profile as shown in FIGS. 2A and 2B, the skilled person will understand that the fins may have the profile as shown in FIGS. 1A and 1B, FIGS. 3A and 3B or another profile.

Figure 6:
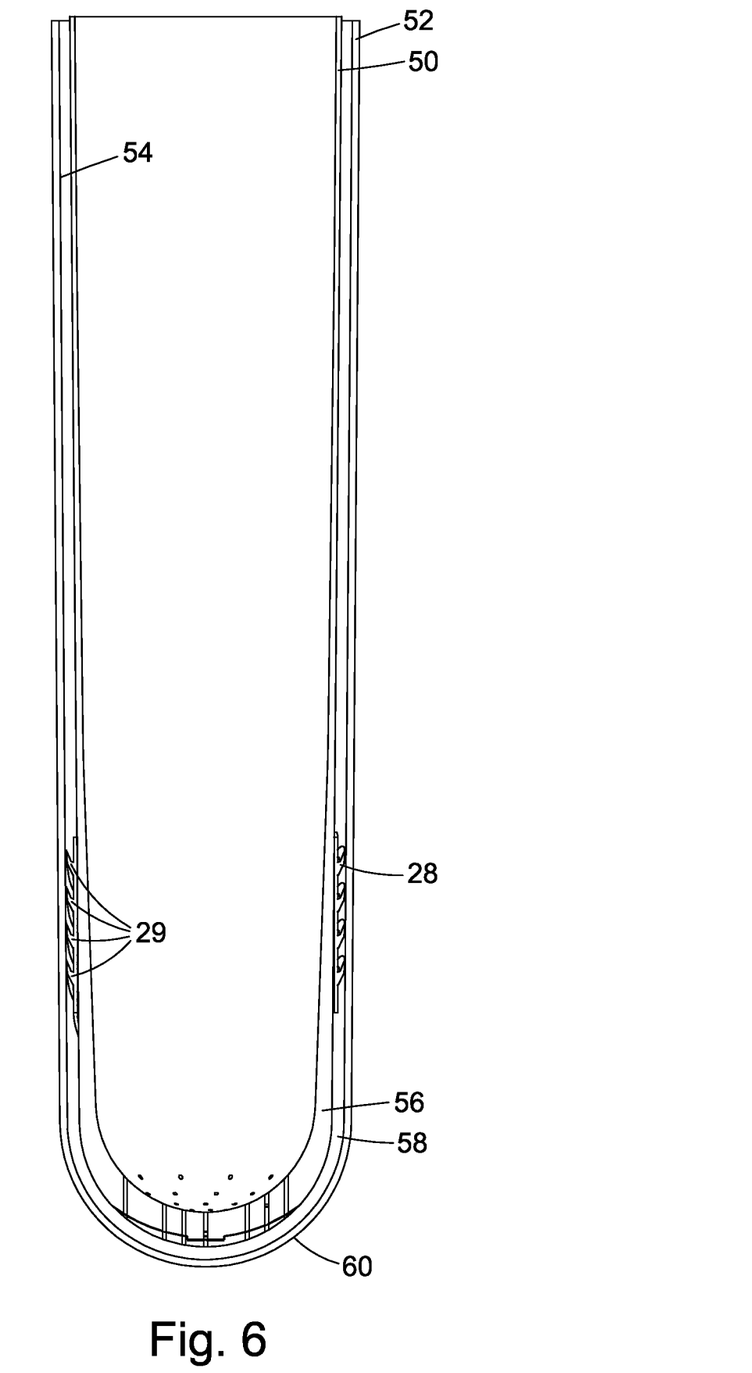
FIG. 6 is a cross-section view of a suspension liner on which is mounted a seal as shown in FIGS. 3A and 3B when inserted into a socket.

FIG. 6 is a cross-section view of a lower part of a suspension liner 50 on which is mounted the seal 28 as shown in FIGS. 3A and 3B when inserted into a socket 52. As can be seen in this Figure, when the liner 50 and seal 28 combination is inserted into the socket 52 the fins 29 push against an interior wall 54 of the socket 52 to seal the distal portion 56 of the liner 50 in the socket 52. Where the socket includes an expulsion valve (not shown) a reduced pressure can be maintained in the cavity 58 formed between the distal portion 56 of the liner 50, the fins 29 and the socket 52. Note that for diagrammatic convenience the volume, and in particular the width, of the cavity 58 is exaggerated in FIG. 6, whereas in practice the volume of this cavity 58 will be minimal in the presence of a reduced pressure when an expulsion valve is used. In other words, the outer surface of the liner 50 will generally abut the inner wall 54 of the socket 52.

It can be seen from FIG. 6 that a feature of the fins 29 having a saw-tooth profile is that the liner 50 and seal 28 combination can be easily inserted into the socket 52 whereas removal of the liner 50 and seal 28 combination from the socket 52 will be impeded by the fins 28 which will be drawn into closer contact by the associated increase in vacuum generated in cavity 58, unless the expulsion valve is opened.

Various modifications will be apparent to those in the art and it is desired to include all such modifications as fall within the scope of the accompanying claims.

In the embodiments described above the fins have either a triangular, a rounded profile or a saw-tooth profile. In other embodiments the fins have other profiles including either solid or inflatable profiles.

In the embodiments described above all of the fins are wavy. In other embodiments one or more, but not all, of the fins may be wavy, i.e., the non-wavy seals may circle straight around the substrate, following a plane passing perpendicular through an axis of the seal/liner.

In the embodiments described above the fins follow a wavy trajectory around the seal substrate or liner. In other embodiments the fins may have straight sections whilst overall reciprocating axially along the substrate or liner.

In the embodiments described above the fins are grouped together and equally spaced over a minority of the length of the liner. In other embodiments there may be a single fin or the plurality of fins may be spaced unequally or the plurality of fins may be spaced along the majority of the length of the liner.

In the embodiments described above both upper and lower edges of the substrate are wavy and run parallel to the fins. In other embodiments one or both of the edges may not run parallel to the fin or fins, e.g., they may be cut straight along a plane running perpendicular to a point along the axis of the substrate.

Rather than incorporating a seal into a seal as described with reference to FIG. 5, the seal may be incorporated into a fabric tube which would allow easier positioning of the tube and seal on a liner.

Similarly, the seal may be incorporated into a sock which is to be placed over a liner whether or not the liner already includes a fabric cover. Such a sock would require a means for sealing the interior of the sock in the region of the seal against the liner, for example by disposing rubber or silicone on the interior of the sock.

When the seal is placed over a liner the inner wall of the seal may seal against the outer wall of the liner to produce an airtight seal. In other embodiments the seal between the inner wall of the seal and the liner outer wall may not be completely airtight. For example, where an external vacuum source is attached to the socket there may be sufficient vacuum produced to allow ingress of some air between the inner wall of the seal and the liner outer wall, where a fabric layer may be deployed. This gentle flow of air over the liner outer surface could be used to cool the limb, for example.

In the present invention the fin or fins which project radially from the substrate of the tubular sleeve or from the body of the liner are used to provide a seal against an interior surface of a socket. In other embodiments, a fin or fins may be provided on an interior surface of the tubular substrate or on an interior surface of the liner body, to improve the seal between the tubular sleeve and the liner and/or between the liner and the skin.

In the embodiments described above the fins have a height of around 5 mm. In alternative embodiments the fins may have a height of between 3 mm and 8 mm, and preferably between 4 mm and 6 mm. In other embodiments the height of the fins may vary as the fins pass around the seal or liner.

In the embodiments described above the fins have a width of around 3 mm. In alternative embodiments the fins may have a width of between 1.5 mm and 5 mm, and preferably between 3 mm and 4 mm. In other embodiments the width of the fins may vary as the fins pass around the seal or liner.

The invention claimed is:

1. A seal for a suspension liner, the seal comprising:
   a tubular substrate having a first open end, a second open end, and an axis; and
   a plurality of discrete endless fins projecting radially from the substrate and running peripherally around the substrate,
   wherein at least one of the fins reciprocates axially as it runs peripherally around the substrate.

2. A seal as claimed in claim 1, wherein all of the fins reciprocate axially as they run peripherally around the substrate.

3. A seal as claimed in claim 1, wherein the fins reciprocate sinusoidally around the substrate.

4. A seal as claimed in claim 1, wherein a plurality of the fins are parallel to each other.

5. A seal as claimed in claim 4, wherein edges of the substrate are parallel to the fins.

6. A seal as claimed in claim 1, wherein at least one of the fins has a triangular profile.

7. A seal as claimed in claim 1, wherein at least one of the fins has a rounded profile.

8. A seal as claimed in claim 1, wherein at least one of the fins has a saw-tooth profile.

9. A seal for a suspension liner, the seal comprising:
   a tubular substrate extending along an axis, wherein the tubular substrate is open at both ends; and
   a plurality of discrete endless fins projecting from the substrate and running circumferentially around the substrate,
   wherein at least one of the fins runs around the substrate and reciprocates between a pair of parallel planes which pass through first and second points along the axis and which are perpendicular to the axis, the first and second points being separated by a distance greater than the width of the at least one fin.

10. A seal as claimed in claim 1, wherein the seal is made from a resiliently elastic material.

11. A suspension liner comprising an elongate, generally frusto-conical or cylindrical body which is closed at a first end and open at a second end, the body bearing a seal as defined in claim 1 at a position between the open and closed ends of the body.

12. A suspension liner as claimed in claim 11, wherein the liner is perforated distal to the fin or fins.

13. A suspension liner as claimed in claim 11, wherein the liner is perforated proximal to the fin or fins.

* * * * *